United States Patent [19]

Pollock et al.

[11] 4,368,139

[45] Jan. 11, 1983

[54] NONDUSTING FREE-FLOWING SOLID PARTICULATE POLYVALENT METAL CARBOXYLIC ACID SALT COMPOSITIONS AND PROCESS FOR PREPARING THE SAME

[75] Inventors: Mark W. Pollock, Teaneck, N.J.; George A. Seubert, Jr., Massapequa Park, N.Y.

[73] Assignee: Argus Chemical Corporation, Brooklyn, N.Y.

[21] Appl. No.: 235,337

[22] Filed: Feb. 17, 1981

[51] Int. Cl.$^3$ .............................................. C09K 3/00
[52] U.S. Cl. ................................... 252/384; 524/114; 252/400 R; 252/407
[58] Field of Search .................. 252/400 R, 407, 384; 260/348.38, 348.58, 348.61, 45.75 R, 23 XA, 45.8 AH; 524/114

[56] References Cited

U.S. PATENT DOCUMENTS

| | | | |
|---|---|---|---|
| 2,590,059 | 3/1952 | Winkler | 524/114 |
| 2,671,064 | 3/1954 | Cowell et al. | 260/45.8 AH |
| 2,875,349 | 10/1958 | Greenspan et al. | 524/114 |
| 2,912,397 | 11/1959 | Houska et al. | 524/114 |
| 3,261,793 | 7/1966 | Stevenson | 260/23 XA |
| 3,558,539 | 1/1971 | Irish | 524/114 |

OTHER PUBLICATIONS

Deanin—"Synergistic Interaction in Zinc/Epoxy Phosphite Stabilization of Polyvinyl Chloride"—Polymer Engineering & Science, vol. 13, No. 2, Mar. 1973, pp. 96–101.

Chevassus—The Stabilization of Polyvinyl Chloride, St. Martin's Press Inc., N.Y., 1963, pp. 130–137, 171 and 172.

Plastics Compounding—Jul./Aug. 1980, pp. 83 to 90.

*Primary Examiner*—Veronica P. Hoke

[57] ABSTRACT

Solid particulate polyvalent metal carboxylic acid salt compositions particularly useful as polyvinyl chloride resin stabilizers are provided comprising at least one solid polyvalent metal carboxylic acid salt in dusting particulate form and a liquid epoxy fatty acid ester having a viscosity at 25° C. within the range from about 100 to about 2000 cps, in an amount within the range from about 3% to about 20% by weight of the total composition, sufficient to render the particulate salt composition substantially nondusting, while maintaining the salt composition free-flowing, non-caking and non-tacky.

10 Claims, No Drawings

NONDUSTING FREE-FLOWING SOLID PARTICULATE POLYVALENT METAL CARBOXYLIC ACID SALT COMPOSITIONS AND PROCESS FOR PREPARING THE SAME

Polyvalent metal salts of carboxylic acids, especially fatty acids, are widely used in polyvinyl chloride resin stabilizer compositions and as commercially available are generally in one of two forms: liquids and solids. The liquid compositions are preferred in many cases, because they are more readily blended with the polymer, and are more easily measured out, at the same time being nondusting. However, they may lower the softening point of the polymer. The solid compositions necessarily must be in free-flowing finely divided form, so that they can be measured out in small quantities, but in such form particles of polyvalent metal fatty acid salts tend to be friable, disintegrate by abrasion into smaller particles, and can thereby become very dusty. This is a serious problem in fabricating and manufacturing plants, because many polyvalent metal fatty acid salts are toxic, particularly the barium and cadmium salts, as well as certain tin salts, and workers therefore must be protected from inhaling or otherwise ingesting air-entrained dusts of such compositions. In addition, many such polyvalent metal fatty acid salts are highly flammable, and in air as dusts can form explosive mixtures capable of demolishing the plant when accidentally ignited by a spark from the machinery or electrical circuitry.

One way of avoiding these difficulties is to convert the solid stabilizer compositions into pastes by addition of an inert solvent or diluent. Pastes are however difficult to work with, and cannot be measured out accurately in small quantities. They also are difficult to blend uniformly in the resin, because of their cohesive tendency, and their slow flow rate, even under pressure and the stress of the mixing equipment.

In accordance with the invention the dusting problem accompanying particulate polyvalent metal carboxylic acid salts is overcome without rendering the particulate material non-free-flowing, caking or tacky by combining therewith a small amount of a liquid epoxy fatty acid ester having a viscosity at 25° C. within the range from about 100 to about 2000 cps. The liquid material in the amount required to overcome dusting is wholly absorbed on the salt particles, thus not interfering with their free-flowing characteristics.

The epoxy fatty acid esters are themselves stabilizers and plasticizers for polyvinyl chloride resins and other synthetic polymers, and consequently in a stabilizer composition are not deleterious. However, the amount required of the epoxy fatty acid ester to impart the nondusting characteristic is very small, well below the amount required for stabilizing and/or plasticizing action on a synthetic resin. Thus, in the amounts employed in the compositions of the invention, the epoxy fatty acid ester cannot be regarded as having the function of either a stabilizer or a plasticizer. Its function is purely physical, to prevent dusting, and it apparently functions in this way by being absorbed on the solid polyvinyl metal carboxylic acid salt particles, thus overcoming their friability, and their tendency to disintegrate into smaller dust-size particles.

The invention accordingly provides nondusting free-flowing solid particulate polyvalent metal carboxylic acid salt compositions comprising at least one solid particulate polyvalent metal carboxylic acid salt in dusting particulate form, and a liquid epoxy fatty acid ester having a viscosity at 25° C. within the range from about 100 to about 2000 cps in an amount within the range from about 3% to about 20% by weight of the salt composition sufficient to render the particulate salt composition substantially nondusting while maintaining the salt composition free-flowing, non-caking and non-tacky.

The compositions are readily prepared by simple blending of the liquid epoxy fatty acid ester in conventional mixing equipment with the solid particulate polyvalent metal carboxylic acid salt.

The invention accordingly also provides a process for rendering solid particulate polyvalent metal carboxylic acid salts nondusting and yet free-flowing, without rendering them caking and tacky, by combining therewith a liquid epoxy fatty acid ester having a viscosity at 25° C. within the range from about 100 to about 2000 cps in an amount within the range from about 3% to about 20% by weight of the salt.

The invention is applicable to polyvalent metal salts of carboxylic acids as a class, but for use as a synthetic resin stabilizer the carboxylic acid will ordinarily have from about six to about twenty-four carbon atoms. The polyvalent metal can be any metal or Group II of the Periodic Table, such as zinc, calcium, cadmium, barium, magnesium and strontium, as well as heavy metals such as tin and lead, and other polyvalent metals such as manganese, iron and nickel.

The carboxylic acid can be any organic non-nitrogenous monocarboxylic acid having from six to twenty-four carbon atoms. The aliphatic, aromatic, alicyclic and oxygen-containing heterocyclic carboxylic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

An exemplary of the acids in the form of their polyvalent metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicyclic acid, naphthoic acid, 1-naphthalene acetic acid, orthobenzoyl benzoic acid, naphthenic acids derived from petroleum, abietic acid, dihydroabietic acid, hexahydrobenzoic acid, methyl furoic acid and toluic acid.

For use as synthetic resin stabilizers, the water-insoluble salts are preferred, because they are not leached out when the resin is in contact with water. These salts are made by the usual types of reactions, such as by mixing the acid or anhydride with the corresponding oxide or hydroxide of the metal in a liquid solvent, and heating, if necessary, until salt formation is complete.

Polyvalent metal carboxylic acid salts are formulated as solid polyvinyl chloride resin stabilizers and as stabilizers for other synthetic resins such as polyolefins, either individually or in admixture with other synthetic resin stabilizers that do not interfere with the nondusting and free-flowing characteristic. Thus the polyvalent metal salts of carboxylic can be combined or mixed with other stabilizers such as organic phosphites, phenolic antioxidants, thiodipropionates, and other known stabilizers, provided they are in solid particulate dusting form.

Any liquid epoxy fatty acid ester or ester mixtures having a viscosity at 25° C. within the range from about 100 to about 2000 cps is effective. Preferably, the viscosity at 25° C. is within the range from about 200 to about 1000 cps. The viscosity of any epoxy fatty acid ester or esters outside this range can be brought within the range by blending with other epoxy fatty acid ester or esters.

Particularly useful are the epoxy higher fatty acid esters having from about three to about one hundred fifty carbon atoms. Such esters will initially have had unsaturation in the alcohol or acid portion of the molecule, which is taken up by the formation of the epoxy group.

Typical unsaturated acids are acrylic, oleic, linoleic, linolenic, erucic, ricinoleic, and brassidic acids, and these may be esterified with organic monohydric or polyhydric alcohols, the total number of carbon atoms of the acid and the alcohol being within the range stated. Typical monohydric alcohols include butyl alcohol, 2-ethyl hexyl alcohol, lauryl alcohol, isooctyl alcohol, stearyl alcohol, and oleyl alcohol. The octyl alcohols are preferred. Typically polyhydric alcohols include pentaerythritol, glycerol, ethylene glycol, 1,2-propylene glycol, 1,4-butylene glycol, neopentyl glycol, ricinoleyl alcohol, erythritol, mannitol and sorbitol. Glycerol is preferred. These alcohols may be fully or partially esterified with the epoxidized acid.

Also useful are the epoxidized mixtures of higher fatty acid esters found in naturally occurring oils, such as epoxidized soybean oil, epoxidized olive oil, epoxidized coconut oil, epoxidized cottonseed oil, epoxidized linseed oil, epoxidized rapeseed oil, epoxidized tung oil, epoxidized fish oil, epoxidized safflower seed oil, epoxidized caster oil, epoxidized corn oil, epoxidized sunflower seed oil, epoxidized perilla oil, epoxidized walnut oil, epoxidized hempseed oil, and epoxidized tallow. Of these, epoxidized soybean oil is preferred.

The alcohol can contain the epoxy group and have a long or short chain, and the acid can have a short or long chain, such as epoxystearyl acetate, epoxystearyl stearate, glycidyl stearate, and polymerized glycidyl methacrylate.

The epoxy fatty acid ester is effective in a small amount. An amount within the range from about 3% to about 20% is quite adequate. Preferably, the amount is within the range from about 5% to about 15%. All amounts are based on the weight of the solid stabilizer composition in which the polyvalent metal carboxylic acid salt or salts are present.

The nondusting particulate polyvalent metal carboxylic acid salt compositions of the invention are particularly suited for formulation into solid particulate synthetic resin stabilizer compositions with other solid particulate stabilizer components.

One preferred class of such stabilizers are the phenolic antioxidants which contain one or more phenolic hydroxyl groups, and one or more phenolic nuclei, and can contain from about either to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl;

$x_1$ and $x_2$ are integers from one to four, and the sum of $x_1$ and $x_2$ does not exceed six.

The polycyclic phenol employed in the stabilizer combination is one having at least two aromatic nuclei linked by a polyvalent linking radical, as defined by the formula:

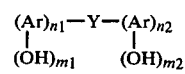

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms;

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar;

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy $$(R'C-O)$$
$$\underset{O}{\|}$$

where R' is aryl, alkyl or cycloalkyl, or thiohydrocarbon groups having from one to about thirty carbon atoms, and carboxyl $$(-C-O-)$$
$$\underset{O}{\|}$$

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluorenyl groups.

When Ar is a benzene nucleus, the polyhydric polycyclic phenol has the structure:

$$\left(\text{OH}\right)_{m_1}\left[\left(\text{OH}\right)_{m_2}\right]\left(\text{OH}\right)_{m_3}$$
(with substituents $(R_1)_{x_1}$, $(R_2)_{x_2}$, $(R_3)_{x_3}$, linked by Y, repeating $y_2$)

wherein $R_1$, $R_2$ and $R_3$ are inert substituent groups as described in the previous paragraph;

$m_1$ and $m_2$ are integers from one to a maximum of five;

$m_2$ is an integer from one to a maximum of four;

$x_1$ and $x_3$ are integers from zero to four; and $x_2$ is an integer from zero to three;

$y_1$ is an integer from zero to about six; and $y_2$ is an integer from one to five, preferably one or two.

Preferably, the hydroxyl groups are located ortho and/or para to Y.

Exemplary Y groups are alkylene, alkylidene, and alkenylene arylene, alkylarylene, arylalkylene, cycloalkylene, cycloalkylidene, and oxa- and thia-substituted such groups; carbonyl groups, tetrahydrofuranes, esters and triazino groups. The Y groups are usually bi, tri, or tetravalent, connecting two, three or four Ar groups. However, higher valency Y groups, connecting more than four Ar groups can also be used. According to their constitution, the Y groups can be assigned to subgenera as follows:

(1) Y groups where at least one carbon in a chain or cyclic arrangement connect the aromatic groups, such as:

$-CH_2-CH_2-$; $-(CH_2)_5-$; $-CH_2-$; $-CH_2-\phi-CH_2-$;

(various cyclic and substituted alkylene linkers shown)

$$\begin{array}{c}CH_3\\-CH-\\CH_3\end{array}; -CH-; -CH-; \begin{array}{c}C_2H_5\\-CH-\\C_2H_5\end{array}; -CH-; -\phi-;$$
(with $C_3H_7$, $C_2H_5$, $CH_3$ substituents)

$$\begin{array}{c}CH_3\\-CH_2-C-CH_2-\\CH_3\end{array}; -CH_2-\phi-CH_2-; -CH_2-\text{(cyclohexyl)}-;$$

$-CH-$; $-CH-$; $-C_2H_4-\phi-$; $-C(CH_3)H-(CH_2)_3-\text{cyclohexyl}(CH_3)-$;
(with phenyl and cyclohexyl substituents)

$-\text{cyclohexyl}-CH_2-\text{cyclohexyl}(C_2H_5)-$; $-\text{cyclohexyl}-\text{cyclohexyl}(CH_3)-$;

(additional complex cyclic structures including tetramethylbenzene-linked, norbornane-type, and $CH_3-CH-\phi(C_4H_9)-OH$ with $CH_3$ substituent)

(2) Y groups where only atoms other than carbon link the aromatic rings, such as: $-O-$, $-S-$, $$-\underset{O}{\overset{}{S}}-, \quad -\underset{O}{\overset{O}{\underset{\|}{S}}}-$$

and $-(S)_x-$ where x is a number from one to ten;

(3) Y groups made up of more than a single atom including both carbon and other atoms linking the aromatic nuclei, such as:

$-CH_2-O-CH_2-$; $\begin{array}{c}-CH-CH_2-O-CH_2-CH-\\CH_3\qquad\qquad\qquad CH_3\end{array}$;

-continued

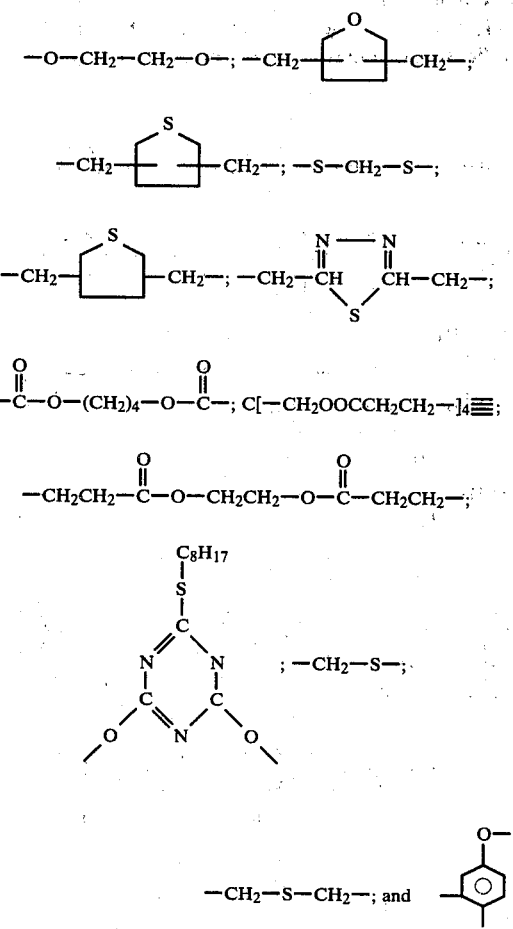

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include gualacol, resorcinol monoacetate, vanillin, butyl salicylate, 2,6-di-tert-butyl-4-methyl phenol, 2-tert-butyl-4-methoxy phenol, 2,4-dimonyl phenol, 2,3,4,5-tetradecyl phenol, tetrahydro-α-naphthol, o-, m- and p-cresol, o-, m- and p-phenyl-phenol, o-, m-and p-xylenols, the carvenols, symmetrical xylenol, thymol, o-, m- and p-nonylphenol, o-, m- and p-dodecyl-phenol, and o-, m- and p-octyl phenol, o-, and m-tert-butyl-p-hydroxy-anisole, p-n-decyloxy-phenol, p-n-decyloxy-cresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol methyl-p-hydroxy benzoate, p-di-chlorobenzoyl-aminophenol, p-hydroxysalicyl anilide, stearyl-(3,5-di-methyl-4-hydroxy-benzyl) thioglycolate, stearyl-β-(4-hydroxy-3,5-di-t-butylphenyl) propionate, distearyl-3,5-di-t-butyl-4-hydroxybenzylphosphonate, and distearyl-(4-hydroxy-3-methyl-5-t-butyl) benzylmalonate.

Exemplary polyhydric phenols are orcinol, propyl gallate, catechol, resorcinol, 4-octyl-resorcinol, 4-dodecyl-resorcinol, 4-octadecyl-catechol, 4-isooctyl-phloroglucinol, pyrogallol, hexahydroxybenzene, 4-isohexyl-catechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)-propane, methylene-bis-(p-cresol), 4,4'-benzylidene bis-(2-tertiary-butyl-5-methyl-phenol), 4,4'-cyclohexylidene bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methyl-benzyl)-4-methylphenol, 4,4'-bis-(2-tertiary-butyl-5-methyl-phenol), 2,2'-bis-(4-hydroxy-phenyl) butane, ethylene bis-(p-cresol), 4,4'-n-butylidene-(2-t-butyl-5-methyl-phenol), 2,2'-methylene-bis-(4-methyl-6-(1'-methyl-cyclohexyl)-phenol), 4,4'-cyclohexylene bis-(2-tertiary-butyl-phenol), 2,6-bis-(2'-hydroxy-3'-t-butyl-5'-methyl-benzyl)-4-methyl-phenol, 1,3'-bis-(naphthalene-2,5-diol)propane, and 2,2'-butylene bis-(naphthalene-2,7-diol), (3-methyl-5-tert-butyl-4-hydroxyphenyl)-4'-hydroxy-phenyl) propane, 2,2'-methylene-bis-(4-methyl-5-isopropylphenol), 2,2'-methylene bis-(5-tert-butyl-4-chlorophenol) (3,5-di-tert-butyl-4-hydroxyphenyl)-(4'-hydroxy-phenyl) ethane, (2-hydroxy-phenyl)-(3', 5'-di-tert-butyl-4', 4-hydroxyphenyl) ethene, 2,2'-methylene bis-(4-octylphenol, 4,4'-propylene bis-(2-tert-butyl-phenol), 2,2'-isobutylene bis-(4-nonylphenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 4,4'-bis-(4-hydroxy-phenyl) pentanoic acid octadecyl ester, cyclopentylene-4,4'-bis-phenol, 2-ethylbutylene-4,4'-bisphenol, 4,4'-cyclooctylene-bis-(2-cyclohexylphenol), β,β-thiodiethanol bis-(3-tert-butyl-4-hydroxyphenoxy acetate), 1,4-butanediol-bis-(3-tert-butyl-4-hydroxyphenoxy acetate), pentaerythritol-tetra-(4-hydroxyphenol propionate), 2,4,4'-tri-hydroxy benzophenone, 4,4'-bis-(4-hydroxy-phenol) pentanoic acid octadecyl thiopropionate ester, 1,1,3-tris-(2'-methyl-4-hydroxy-5'-tert-butylphenyl) butane, 1,1,3-tris-(1-methyl-3-hydroxy-4-tert-butylphenyl) butane, 1,8-bis-(2-hydroxy-5-methylbenzoyl-n-octane, lmethyl-3-(3-methyl-5-tert-butyl-4-hydroxy-benzyl)-naphthalene, 2,2'-(2-butene)-bis-(4-methoxy-6-tert-butyl phenol)-bis-[3,3-bis-(4-hydroxy-3-t-butyplphenyl) butyric acid] glycol ester, 4,4'-butylidene-bis-(6-t-butyl-m-cresol), 1,1,3-tris-(2-methyl-4-hydroxy-5-t-butylphenyl) butane, 1,3,5-tris-(3,5di-t-butyl-4-hydroxybenzyl)-2,4,6-trimethylbenzene, tetrakis[methylene-3-(3,5-di-t-butyl-4-hydroxyphenyl)propionate] methane, 1,3,5-tris-(3,5-di-t-butyl-4-hydroxybenzyl)isocyanurate, 1,3,5-tris-(3,5-di-t-butyl-4-hydroxyphenyl)propionyl-oxyethyl isocyanurate, 2-octylthio-4,6-di-(4-hydroxy-3,5-di-t-butyl) phenoxy-1,3,5-triazine, and pentaerythritol hydroxyphenyl propionate.

A particularly desirable class of polyhydric polycyclic phenols are the dicyclopentadiene polyphenols, which are of the type:

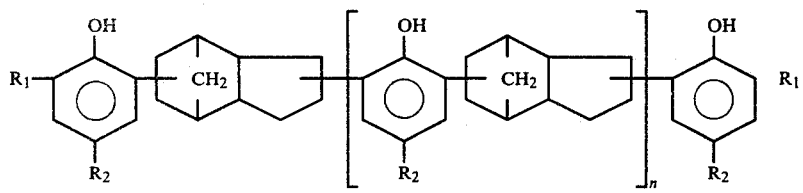

in which

R₁ and R₂ are lower alkyl, and can be the same or different, and n is the number of groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

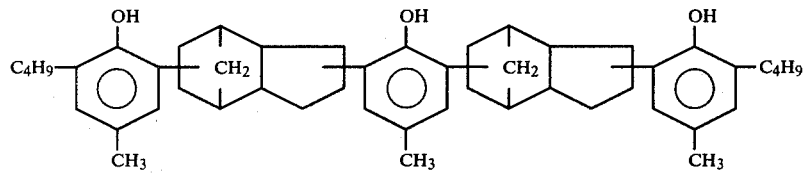

The polyhydric polycyclic phenols used in the invention can also be condensation products of phenol or alkylphenols with hydrocarbons having a bicyclic ring structure and a double bond or two or more double bonds, such as α-pinene, β-pinene, dipentene, limonene, vinylcyclohexane, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus (1). For method of preparation, see e.g., U.S. Pat. Nos. 3,124,555, 3,242,135 and British Pat. No. 961,504.

Another stabilizer component useful with or without a phenolic aliphatic antioxidant is polyhydric alcohol. A variety of polyhydric alcohols can be employed.

The aliphatic polyhydric alcohols have at least two and not more than nine hydroxyl groups and from two to about twenty-four carbon atoms, and include aliphatic carboxylic acid mono and polyesters of such alcohols, having at least two and not more than nine hydroxyl groups and from two to about twenty-four carbon atoms, and ethers of such alcohols having at least two and not more than nine hydroxyl groups, and from two to about twenty-four carbon atoms.

Exemplary polyhydric alcohols are: ethylene glycol, glycerol, erythritol, sorbitol, mannitol, pentaerythritol, glyceryl mono-stearate, glyceryl mono-oleate, ethylene glycol diethyl ether, glyceryl monophenyl ether, neopentylene glycol, dipentaerythritol, tripentaerythritol, bis(trimethylolpropyl) ether, trimethylolpropane, trimethylolethane and trimethylolbutane.

The nondusting polyvalent metal carboxylic acid salt compositions of the invention are especially effective in enhancing the resistance to deterioration by heat and light of polyvinyl chloride resins. The term "polyvinyl chloride" as used herein is inclusive of any polymer formed at least in part of the recurring group:

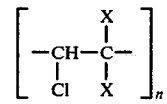

and having chlorine content in excess of 40%. In this group, the X groups can each be either hydrogen or chlorine, and n is the number of such units in the polymer chain. In polyvinyl chloride homopolymers, each of the X groups is hydrogen. Thus, the term includes not only polyvinyl chloride homopolymers but also afterchlorinated polyvinyl chlorides as a class, for example, those disclosed in British Pat. No. 893,288 and the copolymers of vinyl chloride in a major proportion and other copolymerizable monomers in a minor proportion, such as copolymers of vinyl chloride and vinyl acetate, copolymers of vinyl chloride with maleic or fumaric acids or esters, and copolymers of vinyl chloride with styrene. The phosphites are effective also with mixtures of polyvinyl chloride in a major proportion with a minor proportion of other synthetic resins such as chlorinated polyethylene or a copolymer of acrylonitrile, butadiene and styrene.

The compositions are applicable to the stabilization of rigid polyvinyl chloride resin compositions, that is, resin compositions which are formulated to withstand high processing temperatures, of the order of 375° F. and higher, as well as plasticized polyvinyl chloride resin compositions of conventional formulation, even though resistance to heat distortion is not a requisite. Conventional plasticizers well known to those skilled in the art can be employed such as, for example, dioctyl phthalate, octyl diphenyl phosphate and epoxidized soybean oil.

Particularly useful plasticizers are the epoxy higher esters having from 20 to 150 carbon atoms, selected from those named above. Such esters will initially have had unsaturation in the alcohol or acid portion of the molecule, which is taken up by formation of the epoxy group.

The polyvinyl chloride resin can be in any physical form, including, for example, powders, films, sheets, molded articles, foams, filaments, and yarns.

A sufficient amount of the composition is used to enhance the resistance of the polyvinyl chloride to deterioration in physical properties, including, for example, discoloration and embrittlement under the heat and/or light conditions to which the polymer will be subjected. Very small amounts are usually adequate. Amounts within the range from about 0.01 to about 5% by weight of the polyvinyl chloride resin are satisfactory. Preferably, an amount within the range from about 0.05 to about 2% is employed for optimum stabilizing effectiveness.

In addition, any of the conventional polyvinyl chloride resin additives, such as lubricants, emulsifiers, antistatic agents, flame-proofing agents, pigments and fillers, can be formulated as components of the nondusting compositions of the invention.

The nondusting polyvalent metal carboxylic acid salts of the invention are also effective heat stabilizers for olefin polymers such as polyethylene, polypropylene, polybutylene, polypentylene, polyisopentylene, and higher polyolefins.

Olefin polymers on exposure to elevated temperatures undergo degradation, resulting in embrittlement and discoloration.

The stabilizer systems can be employed with any olefin polymer, including low-density polyethylene, high density polyethylene, polyethylenes prepared by the Ziegler-Natta process, polypropylenes prepared by the Ziegler-Natta process, and by other polymerization methods from propylene, poly(butene-1) poly(pentene-1), poly(3-methylbutene-1) poly(4-methyl-pentene-1), polystyrene, and mixtures of polyethylene and polypropylene with other compatible polymers, such as mixtures of polyethylene and polypropylene, and copolymers of such olefins, such as copolymers of ethylene, propylene, and butene, with each other and with other copolymerizable monomers. The term "olefin polymer" encompasses both homopolymers and copolymers.

Polypropylene solid polymer can be defined in a manner to differentiate it from other polyolefins as having a density within the range from 0.86 to 0.91, and a melting point above 150° C. The compositions of the invention are applicable to all such polypropylenes, as distinguished from polypropylenes in the liquid form or in semi-liquid of gel-like forms, such as are used as greases and waxes.

The compositions of the invention are applicable to polypropylenes prepared by any of the various procedures, for the molecular weight and tacticity are not factors affecting this stabilizer system. Isotactic polypropylene, available commercially under the trade name PRO-FAX, and having a softening or hot-working temperature of about 350° F., is an example of a sterically regular polypropylene polymer.

Mixtures of polypropylene with other compatible polymers and copolymers of propylene with copolymerizable monomers not reactive with the phosphite or stabilizer combination can also be stabilized, for example, mixtures of polyethylene and polypropylene, and copolymers of propylene and ethylene.

The compositions are also effective to enhance the resistance to heat degradation of polystyrene; polydienes, such as polybutadiene and polyisoprene; and copolymers of olefins and dienes with other ethylenically and acetylenically unsaturated monomers, such as ethylene-vinyl acetate copolymer, styrene-butadiene copolymers, acrylonitrile-styrene-butadiene copolymers, synthetic rubbers of all types, such as polychloroprene; polyvinylidene chloride; and copolymers of vinyl chloride and vinylidene chloride; vinylidene chloride and vinyl acetate; and other ethylenically unsaturated monomers.

The synthetic polymer can be in any physical form, including (for example) filaments, yarns, films, sheets, molded articles, latex and foam.

A sufficient amount of the stabilizer combination is used to improve the resistance of the synthetic polymer to deterioration in physical properties, including, for example, discoloration, reduction in melt viscosity and embrittlement, under the conditions to which the polymer will be subjected. Very small amounts are usually adequate. Amounts within the range from about 0.001 to about 5% total stabilizers by weight of the polymer are satisfactory. Preferably, from 0.01 to 3% is employed, for optimum stabilization.

The compositions of the invention can be employed in combinations with other conventional heat and light stabilizers for the particular polymer.

Thus, for example, for olefin polymers there can be employed fatty acid salts of polyvalent metals, phenolic antioxidants, and the higher fatty acid esters of thiodipropionic acids, such as, for example, dilauryl thiodipropionate.

With synthetic rubbers and acrylonitrile-butadiene-styrene terpolymers, phenolic antioxidants can be used.

In addition, other conventional additives for synthetic polymers, such as plasticizers, lubricants, emulsifiers, antistatic agents, flame-proofing agents, pigments and fillers, can be employed.

The stabilizer combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples in the opinion of the inventors represent preferred embodiments of the invention:

EXAMPLES 1 AND 2

Compounded Ba-Cd stabilizer, 200 grams, (cadmium laurate, 53%, barium laurate, 27% pentaerythritol, 14% and Bisphenol A, 6%) was agitated in variable-speed household blender at low speed, while epoxidized soybean oil was poured in slowly. The agitation produced much dust at first, and the addition of the epoxidized oil was stopped when the dust had nearly disappeared. It was then determined that 14 grams of epoxidized soyabean oil had been added resulting in a free-flowing and substantially nondusting composition of 49.5% cadmium laurate, 25.2% barium laurate, 13.8% pentaerythritol, 5.6% Bisphenol A and 6.4% epoxidized soybean oil.

200 grams of the same stabilizer as in Example 1 was blended with 20 g epoxidized soybean oil. The product was free-flowing and dust free, and contained 9.1% epoxidized soybean oil.

450 gram samples of the composition of Examples 1 and 2 above were mixed in a HOBART N50 mixer having a 3.5 liter bowl to determine how long the free-flowing and dust-free characteristics were maintained. Agitation was interrupted periodically to examine the condition of the samples. Both compositions were dust-free and free-flowing after 20 minutes. Composition 1 was still dust-free and free-flowing after 60 minutes of mixing. Composition 2 had formed a deposit of caked material on the walls of the bowl after 40 minutes of mixing.

The experiment in the HOBART mixer was repeated with the same stabilizer and 5% of added epoxidized soybean oil. The mixture was dusty after 20 minutes of mixing, somewhat dusty and also lumpy after 40 minutes and dust-free and free-flowing after 60, 80 and 100 minutes. After 120 minutes, the mixture began to cake on the walls of the bowl.

The results show that the stabilizer can be made dust-free and free-flowing by mechanical treatment with epoxidized soybean oil, with an adequate margin of safe operation that avoids overprocessing the product. It is evident that the dust-free composition can be suitably made with 5 to 10% of added epoxidized soybean oil.

EXAMPLE 3

In a Marion mixer having a semicylindrical mixing container and mixing blades mounted on a horizontally installed rotating shaft driven by a motor on the outside of the container, was charged 11,338 g of the same stabilizer as in Example 1, and 853 g (7% by weight) epoxidized soybean oil, and mixing was interrupted every 20 minutes to permit inspection. The mixture became dust-free and free-flowing after 120 minutes of mixing, and remained so until 210 minutes of mixing, when the first signs of caking were observed.

In an experiment similar to Example 3, the epoxidized soybean oil was replaced by an equal quantity of di-2-ethylhexyl phthalate (DOP). After 20 minutes of mixing, the mixture was dust-free but no longer free-flowing. When the quantity of DOP was reduced to 4%, the mixture was still slightly dusty at 80 minutes, and dust-free but caked at 100 minutes. This shows that DOP is unsatisfactory as a dust suppressant.

In similar experiments a C7-C9 linear alkyl phthalate (Santicizer 711), a mineral oil, and epoxidized isooctyl tall oil fatty acid ester were shown to be unsatisfactory at the 4, 5, 6, and 7% levels.

EXAMPLE 4

In a Marion mixer having a semicylindrical mixing container and mixing blades mounted on a horizontally installed rotating shaft driven by a motor on the outside of the container was charged 11338 g of compounded Ba-Cd stabilizer (cadmium stearate, 53%, barium stearate, 27%, pentaerythritol, 14% and Bisphenol A, 6%) and 853 g (7% by weight) epoxidized soybean oil, and mixing was interrupted every 20 minutes to permit inspection. The mixture became dust-free and free-flowing after 160 minutes of mixing, and remained so until 300 minutes of mixing, when the first signs of caking were observed.

EXAMPLE 5

The Marion mixer was charged with 11338 grams of a combination stabilizer made up of 47.5% barium stearate, 47.5% lead stearate, and 5% bisphenol A, and with 1121 grams (9% by weight) epoxidized soybean oil. The mixture became dust-free and free-flowing after 140 to 160 minutes of mixing, and remained so until 200 minutes of mixing. By 220 minutes the motor load had begun to increase.

In a similar experiment in which 11% of epoxidized soybean oil was used, the mixture became dust-free and free-flowing between 100 and 120 minutes, and remained so until about 150 minutes, when it began to cake.

EXAMPLE 6

The Marion mixer was used to combine 11338 grams of combination stabilizer made up of 26% barium stearate, 13% cadmium stearate, 28% zinc stearate, 3% Bisphenol A, and 30% calcined clay, with 1250 g of epoxidized soybean oil. The mixture became dust-free after mixing for 60 minutes, and remained so for 280 minutes without change. This shows that the method is applicable to stabilizers containing an inorganic ingredient.

EXAMPLE 7

Marion mixer experiments were carried out with a combination stabilizer made up of 40% cadmium laurate, 10% cadmium stearate, 20% barium laurate, 19% barium stearate, and 11% Bisphenol A, with various proportions of epoxidized soybean oil. A 9% by weight level in the mixture gave the best results; a dust-free and free-flowing product was obtained after 160 minutes and remained so for over 200 minutes, while at 220 the load on the motor began to increase. Satisfactory mixtures were also obtained with 7% and 10% epoxidized soybean oil.

A mixture with 10% nonylphenol instead of epoxidized soybean oil was unsatisfactory.

EXAMPLE 8

A 500 gram sample of barium laurate and 500 g of barium stearate were each made dust-free and free-flowing by mixing in the HOBART N50 mixer with 15% by weight of epoxidized soybean oil.

EXAMPLE 9

A 500 gram sample of combination stabilizer made up of 60% barium laurate and 40% cadmium laurate was made dust-free and free-flowing by mixing in the HOBART N50 mixer with 6% by weight of epoxidized soybean oil.

EXAMPLE 10

Marion mixer experiments were carried out with a combination stabilizer made up of 53% cadmium laurate, 27% barium laurate, 14% pentaerythritol, and 6%, 2,6-di-t-butyl-p-cresol, along with various proportions of epoxidized soybean oil. Concentrations of 5%, 6%, and 7% epoxidized soybean oil in the mixture were satisfactory, with the 6% level the best.

EXAMPLE 11

A stabilizer made up of 85% zinc stearate and 15% sorbitol was treated in the HOBART N50 mixer with various proportions of epoxidized soybean oil. A mixture containing 5% of the epoxide remained dusty after mixing for 1 hour, while 9% and 10% concentrations gave dust-free and free-flowing products.

EXAMPLE 12

A dust-free and free-flowing mixture was prepared in the Marion mixer from 853 grams epoxidized soybean oil, 90 grams high-surface silica (Hi-Sil 233), 3515 grams barium stearate, 1700 grams cadmium laurate, 3515 grams cadmium 12-hydroxystearate. 1474 grams pentaerythritol, and 1134 grams BHT antioxidant. A satisfactory product was obtained after 70 minutes of mixing, and not adversely affected by continuing to mix for up to 100 minutes.

EXAMPLE 13

A substantially nondusting and free-flowing stabilizer composition was prepared by blending the following ingredients:

| | |
|---|---|
| Barium p-t-butylbenzoate | 157 grams |
| Barium laurate | 50 |
| Cadmium laurate | 67 |
| Bisphenol A | 80 |
| High-surface airborne silica | 3 |
| Calcium carbonate (precipitated) | 617 |
| Epoxidized soybean oil | 116 |

Having regard to the foregoing disclosure, the following is claimed as the inventive and patentable embodiments thereof:

1. Nondusting free-flowing solid particulate polyvalent metal carboxylic acid salt compositions comprising at least one solid particulate polyvalent metal carboxylic acid salt in dusting particulate form, and a liquid epoxy fatty acid ester having a viscosity at 25° C. within the range from about 100 to about 2000 cps in an amount within the range from about 3% to about 20% by weight of the salt composition sufficient to render the particulate salt composition substantially nondusting while maintaining the salt composition free-flowing non-caking and non-tacky.

2. Nondusting free-flowing solid particulate polyvalent metal carboxylic acid salt compositions according to claim 1 in which the polyvalent metal salt is of an aliphatic, aromatic or cycloaliphatic carboxylic acid having from about six to about twenty-four carbon atoms.

3. Nondusting free-flowing solid particulate polyvalent metal carboxylic acid salt compositions according to claim 1 in which the polyvalent metal is a metal of Group II of the Periodic Table.

4. Nondusting free-flowing solid particulate polyvalent metal carboxylic acid salt compositions according to claim 1 in which the polyvalent metal is a heavy metal.

5. Nondusting free-flowing solid particulate polyvalent metal carboxylic acid salt compositions according to claim 1 in which the liquid epoxy fatty acid ester is an epoxy higher fatty acid ester having from about three to about one hundred and fifty carbon atoms.

6. Nondusting free-flowing solid particulate polyvalent metal carboxylic acid salt compositions according to claim 5 in which the epoxy fatty acid ester is epoxidized soybean oil.

7. A process for rendering solid particulate polyvalent metal carboxylic acid salts nondusting and yet free-flowing, without rendering them caking and tacky, which comprises combining thereof a liquid epoxy fatty acid ester having a viscosity at 25° C. within the range from about 100 to about 2000 cps in an amount within the range from about 3% to about 20% by weight of the salt composition.

8. A process according to claim 7 in which the liquid epoxy fatty acid ester is epoxidized soybean oil.

9. Nondusting free-flowing solid particulate polyvinyl chloride resin stabilizer compositions according to claim 1 comprising the polyvalent metal carboxylic acid salt together with another polyvinyl chloride resin stabilizer.

10. Nondusting free-flowing solid particulate polyvinyl chloride resin stabilizer compositions according to claim 9 in which the other stabilizer is selected from the group consisting of polyhydric alcohols, polyhydric alcohol esters and polyhydric alcohol ethers having from two to about nine hydroxyl groups, phenolic antioxidants and epoxy fatty acid esters.

* * * * *